(12) United States Patent
Furuta et al.

(10) Patent No.: US 8,890,553 B2
(45) Date of Patent: Nov. 18, 2014

(54) METHOD OF AND APPARATUS FOR DETECTING CRACKS IN PIEZOELECTRIC ELEMENT

(75) Inventors: Eijiro Furuta, Aikoh-gun (JP); Hajime Arai, Aikoh-gun (JP)

(73) Assignee: NHK Spring Co., Ltd., Kanagawa (JP)

( * ) Notice: Subject to any disclaimer, the term of this patent is extended or adjusted under 35 U.S.C. 154(b) by 293 days.

(21) Appl. No.: 13/287,840

(22) Filed: Nov. 2, 2011

(65) Prior Publication Data

US 2012/0146671 A1 Jun. 14, 2012

(30) Foreign Application Priority Data

Dec. 9, 2010 (JP) ................................. 2010-274270

(51) Int. Cl.
*G01R 29/22* (2006.01)
*G01N 27/02* (2006.01)

(52) U.S. Cl.
CPC ...................................... *G01N 27/02* (2013.01)
USPC ........... 324/727; 324/525; 324/557; 324/693; 324/719; 324/799

(58) Field of Classification Search
CPC ........ G01R 27/28; G01R 23/00; G01N 19/00; G01N 27/20
USPC ......................... 324/727, 652, 525, 557, 693; 360/78.05; 310/318; 73/1.15
See application file for complete search history.

(56) References Cited

U.S. PATENT DOCUMENTS

| | | | | |
|---|---|---|---|---|
| 5,969,532 A | * | 10/1999 | Usui et al. | 324/557 |
| 6,008,564 A | * | 12/1999 | Takayoshi et al. | 310/318 |
| 6,480,010 B2 | * | 11/2002 | Ikuta et al. | 324/727 |
| 6,597,541 B2 | * | 7/2003 | Nishida et al. | 360/294.4 |
| 6,986,564 B2 | * | 1/2006 | Matsuo et al. | 347/68 |
| 7,768,276 B2 | * | 8/2010 | Yao | 324/727 |
| 8,335,049 B1 | * | 12/2012 | Liu et al. | 360/78.05 |
| 2002/0024346 A1 | | 2/2002 | Ikuta et al. | |
| 2006/0220498 A1 | * | 10/2006 | Kremer | 310/338 |
| 2009/0002541 A1 | * | 1/2009 | Niwamae | 348/335 |
| 2009/0287086 A1 | * | 11/2009 | Hyuga | 600/459 |

FOREIGN PATENT DOCUMENTS

| | | |
|---|---|---|
| CN | 101174415 | 5/2008 |
| JP | 6-003305 | 1/1994 |
| JP | 8-211115 | 8/1996 |
| JP | 2001-033415 | 2/2001 |
| JP | 2001-242110 | 9/2001 |
| JP | 2002-184140 | 6/2002 |

(Continued)

*Primary Examiner* — Arleen M Vazquez
*Assistant Examiner* — Neel Shah
(74) *Attorney, Agent, or Firm* — Jordan and Hamburg LLP (57) ABSTRACT

A method detects one or more cracks in a piezoelectric element interposed between a pair of electrodes and deforms according to a voltage applied thereto through the pair of electrodes. The method includes steps of applying a voltage at least at a resonance frequency of the piezoelectric element to the piezoelectric element through the pair of electrodes, measuring a dielectric tangent between the pair of electrodes under the applied voltage, and detecting if there are cracks in the piezoelectric element according to the measured dielectric tangent. The dielectric tangent of the piezoelectric element at the resonance frequency has a large peak or no peak depending on whether or not the piezoelectric element has cracks. Accordingly, the method easily and surely detects if the piezoelectric element has cracks according to the dielectric tangent of the piezoelectric element measured at the resonance frequency.

14 Claims, 10 Drawing Sheets

(56) References Cited

FOREIGN PATENT DOCUMENTS

| | | | |
|---|---|---|---|
| JP | 2002-257770 | 9/2002 | |
| JP | 2002-367306 | 12/2002 | |
| JP | 2008128875 | * 6/2008 | ............ G01S 7/521 |
| SU | 1790762 | 1/1993 | |

* cited by examiner

Without cracks

Fig.9

With cracks

Fig.10

With microcracks

Fig.11

| Without cracks | Dielectric tangent [−] |
|---|---|
| OK_01 | 10.185 |
| OK_02 | 23.680 |
| OK_03 | 31.882 |
| OK_04 | 49.859 |
| OK_05 | 31.712 |

Fig.12

| With cracks | Dielectric tangent [−] |
|---|---|
| NG_01 | 1.895 |
| NG_02 | 0.500 |
| NG_03 | 1.969 |
| NG_04 | 4.547 |
| NG_05 | 1.257 |

Fig.13

| With microcracks | Dielectric tangent [−] |
|---|---|
| NS_01 | 3.278 |
| NS_02 | 3.045 |
| NB_01 | 1.643 |
| NB_02 | 1.388 |
| NB_03 | 1.697 |
| NB_04 | 0.593 |

Fig.14

METHOD OF AND APPARATUS FOR DETECTING CRACKS IN PIEZOELECTRIC ELEMENT

BACKGROUND OF THE INVENTION

1. Field of the Invention

The present invention relates to a method of and an apparatus for detecting cracks in a piezoelectric element that deforms according to a voltage applied thereto.

2. Description of Related Art

Small-sized, precision information devices are rapidly advancing, and for use with such devices, needs for micro-actuators capable of conducting positioning control for very small distances are increasing. The micro-actuators are highly needed by, for example, optical systems for correcting focuses and inclination angles, ink-jet printers for controlling ink heads, and magnetic disk drives for controlling magnetic heads.

The magnetic disk drives increase storage capacity by increasing the number of tracks per inch (TPI), i.e., by narrowing the width of each track on a magnetic disk.

Large-capacity magnetic disk drives, therefore, need an actuator capable of precisely positioning the magnetic head within a minute range across tracks.

To meet the need, Japanese Unexamined Patent Application Publication No. 2002-184140 proposes a head suspension employing a dual actuator system. The dual actuator system uses a piezoelectric actuator in addition to a usual voice coil motor that drives a carriage to which the head suspension is attached. The piezoelectric actuator includes a piezoelectric element and is arranged between a base plate and a load beam of the head suspension.

In addition to moving a magnetic head of the head suspension with the voice coil motor, the head suspension employing the dual actuator system finely moves the magnetic head in a sway direction (a width direction of the head suspension) with the piezoelectric element that deforms in response to a voltage applied thereto, thereby precisely positioning the magnetic head on a magnetic disk in the magnetic disk drive.

The magnetic disk drive is required to be small and thin, and accordingly, the piezoelectric element is required to be thin.

A thin piezoelectric element easily causes microcracks due to external force applied thereto during production or assembling into a head suspension. The piezoelectric element having microcracks deteriorates a long-term reliability, and therefore, must be discarded as a defective.

The microcracks, however, are difficult to find by external observation with a stereomicroscope. Furthermore, the surface of the piezoelectric element is plated with gold to form electrodes, and therefore, finding microcracks by appearance is hardly achievable.

The microcracks are also undetectable by measuring electric characteristics of the piezoelectric element. When assembled in a head suspension, the piezoelectric element is tested and evaluated by measuring the capacitance thereof. The microcracks, however, cause no change in the capacitance of the piezoelectric element.

To deal with this, Japanese Unexamined Patent Application Publications No. H06-003305 and No. 2002-367306 disclose a technique of examining the impedance-frequency pattern or phase-frequency pattern of a piezoelectric element, or testing the optical transmissivity of a piezoelectric element.

These related arts, however, are unable to easily detect microcracks in the piezoelectric element, or are difficult to achieve in practice. Namely, the related arts are unable to surely find out cracks including microcracks in a piezoelectric element in practice. As a result, most related arts concentrate on preventing cracks from being formed in piezoelectric elements.

SUMMARY OF THE INVENTION

An object of the present invention is to provide a method of and an apparatus for surely detecting one ore more cracks in a piezoelectric element.

In order to accomplish the object, an aspect of the present invention provides a method of detecting one or more cracks in a piezoelectric element interposed between a pair of electrodes and deforms according to a voltage applied thereto through the pair of electrodes. The method includes steps of applying a voltage at least at a resonance frequency of the piezoelectric element to the piezoelectric element through the pair of electrodes, measuring a dielectric tangent between the pair of electrodes under the applied voltage, and detecting if there are cracks in the piezoelectric element according to the measured dielectric tangent.

The dielectric tangent of the piezoelectric element under the voltage at the resonance frequency greatly differs depending on whether or not the piezoelectric element has cracks. Accordingly, based on the dielectric tangent measured under the voltage at the resonance frequency, this aspect of the present invention surely and easily detects if the piezoelectric element has cracks.

BRIEF DESCRIPTION OF THE DRAWINGS

FIGS. 7A and 7B are graphs illustrating an impedance characteristic pattern and a dielectric tangent characteristic pattern of piezoelectric elements with respect to frequencies including a resonance frequency, in which FIG. 7A is without cracks and FIG. 7B is with cracks;

DETAILED DESCRIPTION OF EMBODIMENTS

Embodiments of the present invention will be explained in detail with reference to the drawings. Each embodiment applies a voltage at a resonance frequency of a piezoelectric element through electrodes between which the piezoelectric element is interposed, measures a dielectric tangent between the electrodes under the applied voltage, and according to the measured dielectric tangent, detects if the piezoelectric element has one or more cracks (hereinafter simply referred to as "cracks").

Figure 1:
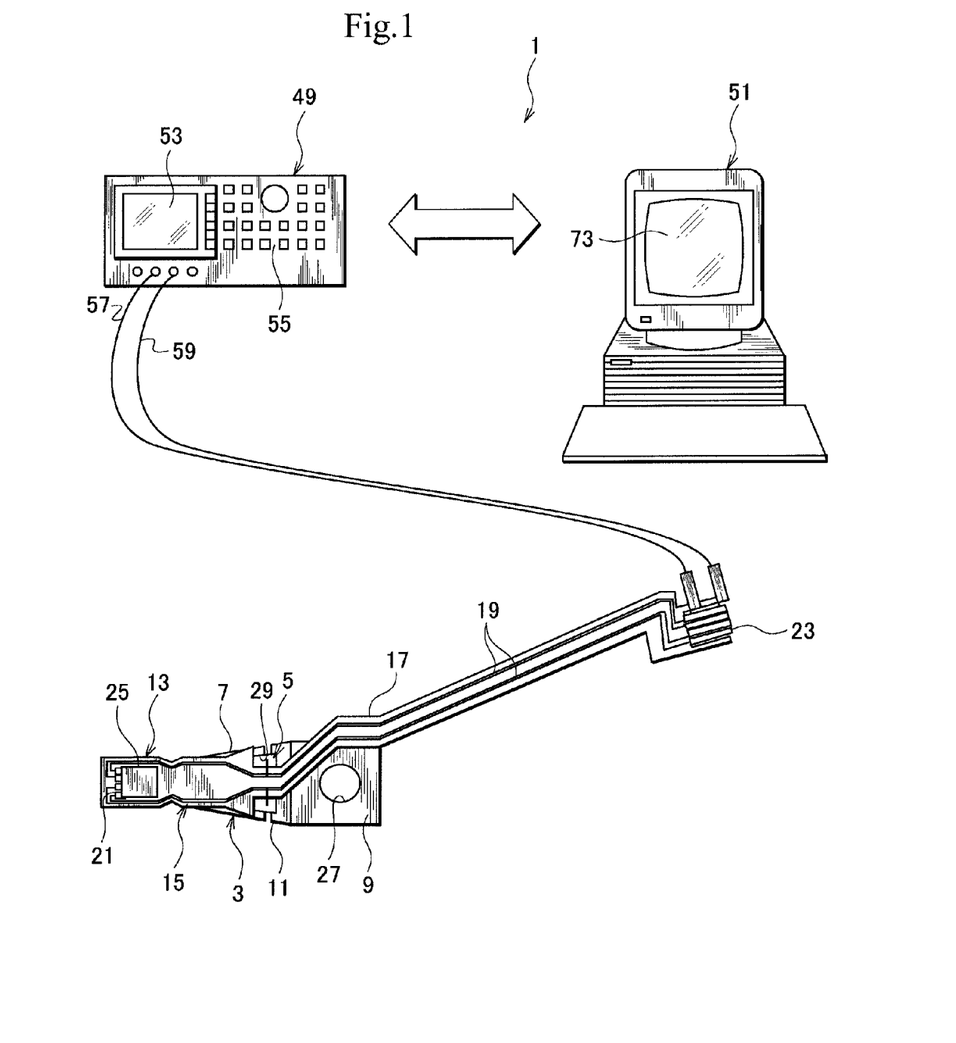
FIG. 1 is a schematic view illustrating an apparatus for detecting cracks in a piezoelectric element according to a first embodiment of the present invention and a head suspension in which the piezoelectric element is arranged.

FIG. 1 is a schematic view illustrating an apparatus for detecting cracks in a piezoelectric element according to the first embodiment of the present invention as well as a head suspension 3.

In FIG. 1, the crack detecting apparatus 1 detects if a piezoelectric element 5 assembled in a head suspension 3 has cracks. First, an example of the piezoelectric element 5 and head suspension 3 will be explained.

The head suspension 3 has a load beam 7 as a driven part, a base plate 9 as a base part, and a piezoelectric actuator 11.

The load beam 7 applies load onto a head 13 that is arranged at a front end of the load beam 7. The load beam 7 is made of, for example, a resilient metal thin plate such as a resilient stainless steel thin plate and has a thickness in the range of, for example, about 30 to 150 µm. The load beam 7 has a flexure 15 as a wiring member.

The flexure 15 includes a conductive thin plate 17 that is made of, for example, a resilient thin stainless steel (SST) rolled plate, an insulating layer formed on the conductive thin plate, and a wiring pattern 19 formed on the insulating layer. The wiring pattern 19 includes signal transmission wires and power supply wires. A first end of the wiring pattern 19 has terminals 21 and a second end thereof has terminals 23.

A front end of the flexure 15 supports a slider 25 of the head 13. The slider 25 is electrically connected to the terminals 21 at the first end of the wiring pattern 19.

A base end of the load beam 7 is supported with the base plate 9. The base plate 9 is made of, for example, a metal thin plate such as a stainless steel thin plate and has a thickness in the range of about 150 to 200 µm.

The base plate 9 has a circular boss 27. Through the boss 27, the base plate 9 is fitted to a carriage (not illustrated) that is turned by a voice coil motor (not illustrated). Between the base plate 9 and the load beam 7, the piezoelectric actuator 11 having the piezoelectric element 5 is arranged.

When the piezoelectric element 5 deforms according to or in response to a voltage applied thereto, the piezoelectric actuator 11 that contains the piezoelectric element 5 drives the load beam 7 for a very small distance in a sway direction (width direction of the load beam 7).

The piezoelectric element 5 is made of piezoelectric ceramics such as PZT (lead zirconate titanate) and substantially has a rectangular shape. The thickness of the piezoelectric element 5 is in the range of, for example, about 70 to 200 µm. The piezoelectric element 5 is fitted with a nonconductive adhesive into an opening 29 formed between the load beam 7 and the base plate 9.

Figure 2:
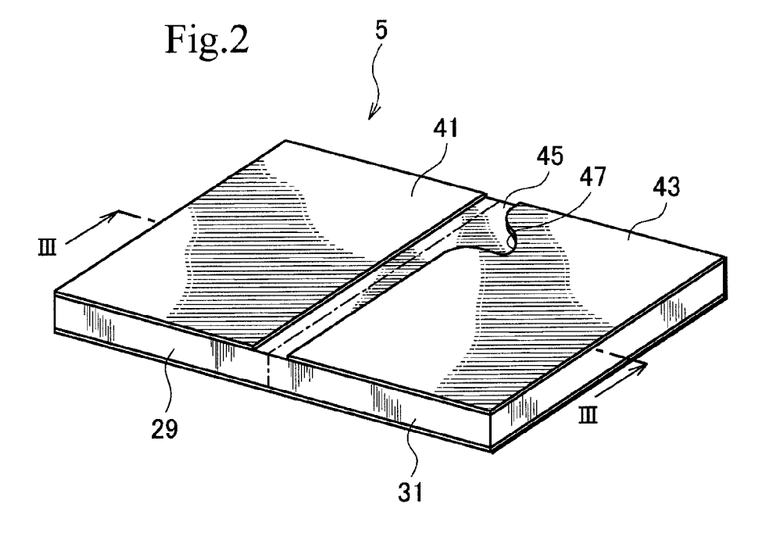
FIG. 2 is a perspective view illustrating the piezoelectric element of FIG. 1.
Figure 3:
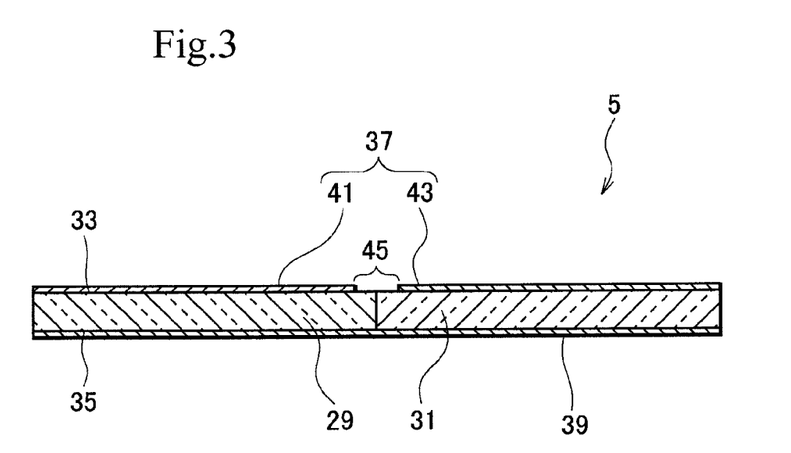
FIG. 3 is a sectional view taken along a line of FIG. 2.

FIG. 2 is a perspective view illustrating the piezoelectric element 5 and FIG. 3 is a sectional view taken along a line of FIG. 2.

In FIGS. 2 and 3, the piezoelectric element 5 includes piezoelectric bodies 29 and 31 that are divided from each other, are arranged side by side in a width direction (left-right direction) of piezoelectric actuator 11, and are differently polarized in 180-degree directions. Incidentally, the piezoelectric actuator 11 and load beam 7 are the components of the head suspension 3, and therefore, the width or lateral directions of the piezoelectric actuator 11 and load beam 7 correspond to a width or lateral direction of the head suspension 3. First and second surfaces 33 and 35 of the piezoelectric element 5 are provided with electrodes 37 and 39, respectively. The piezoelectric element 5 is interposed between the electrodes 37 and 39.

The electrodes 37 and 39 each are made of a conductive metal plate such as a gold (Au) plate that is made by vapor deposition, spattering, plating, metal paste, or the like.

The electrode 37 on the first surface 33 of the piezoelectric element 5 includes electrode parts 41 and 43 formed on the piezoelectric bodies 29 and 31, respectively. The electrode parts 41 and 43 are grounded through conductive resin such as silver paste to the load beam 7.

The electrode parts 41 and 43 are separated from each other with a gap 45. The electrode part 43 has a recess 47 that is continuous to the gap 45. The recess 47 is used to distinguish, by its shape, a polarity of the electrode 37 on the piezoelectric element 5.

The electrode 39 on the second face 35 of the piezoelectric element 5 serves as a common electrode with respect to the electrode 37 (41, 43). As illustrated in FIG. 1, the electrode 39 is electrically connected through, for example, a bonding wire to the wiring pattern 19 of the flexure 15.

The above-identified dimensions, configurations and the like of the head suspension 3 and piezoelectric element 5 are the examples for an explanation of the method of detecting cracks of the piezoelectric element 5 according to the embodiment of the present invention. Other dimensions, configurations and the like of the head suspension 3 and piezoelectric element 5 may be employed to carry out the method of the present invention.

Figure 4:
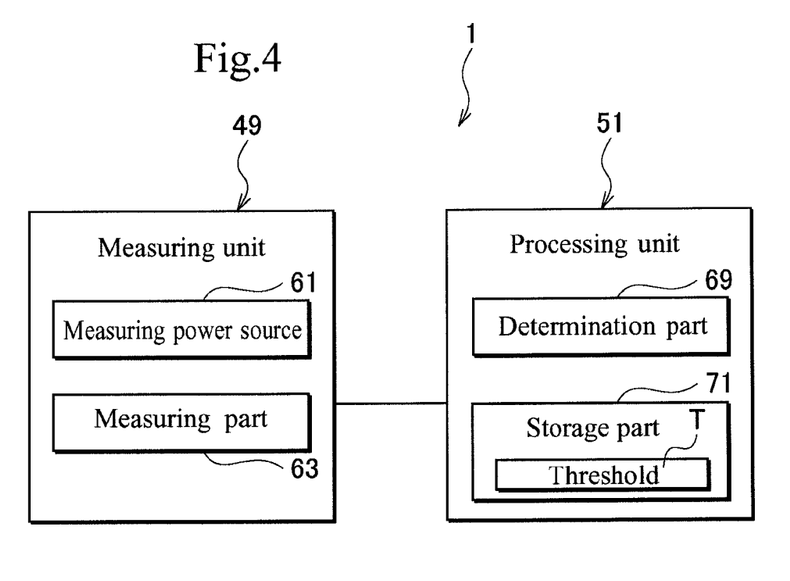
FIG. 4 is a block diagram roughly illustrating the crack detecting apparatus of FIG. 1.

FIG. 4 is a block diagram roughly illustrating the crack detecting apparatus 1 of FIG. 1. In FIGS. 1 and 4, the crack detecting apparatus 1 includes a measuring unit 49 and a processing unit 51 as a detecting unit.

The measuring unit 49 is, for example, an LCR meter and includes a display 53, a control panel 55, measuring cables 57 and 59, and the like. The measuring unit 49 is connected through the measuring cables 57 and 59 to the terminals 23 at the second end of the wiring pattern 19 of the flexure 15. The measuring unit 49 contains a measuring power source 61 as a voltage applying unit and a measuring part 63.

The measuring power source 61 applies, through the measuring cables 57 and 59, a measuring voltage at a set frequency to the electrodes 37 and 39 of the piezoelectric element 5. The measuring voltage is, for example, 500 mV and the frequency thereof is changed in the range of, for example, 100 Hz to 2 MHz at intervals of 5 kHz.

Accordingly, the measuring power source 61 is capable of applying a voltage at least at a resonance frequency of the piezoelectric element 5 to the piezoelectric element 5 through the pair of the electrodes 37 and 39.

The measuring part 63 measures, according to a current passing when a measuring voltage is applied to the piezoelectric element 5, a dielectric tangent tan δ between the electrodes 37 and 39. The measuring part 63 is capable of measuring a dielectric tangent between the electrodes 37 and 39 at a resonance frequency of the piezoelectric element 5. The measured dielectric tangent is sent to the processing unit 51.

The processing unit 51 is an information processing unit such as a personal computer and includes a determination part 69 and a storage part 71. The determination part 69 includes, for example, a CPU and is launched by executing a program stored in the storage part 71.

The determination part 69 compares the measured dielectric tangent from the measuring unit 49 with a threshold T stored in the storage unit 71. If the measured dielectric tangent is lower than the threshold T, the determination part 69 determines that the piezoelectric element 5 has cracks. A result of the determination made by the determination part 69 is displayed on a monitor 73 of the processing unit 51.

The threshold T is set between a dielectric tangent (peak value) measured at a resonance frequency on piezoelectric element samples without cracks and a dielectric tangent (peak value) measured at the resonance frequency on piezoelectric element samples with cracks. According to the first embodiment, the threshold T is 10.

Figure 5:
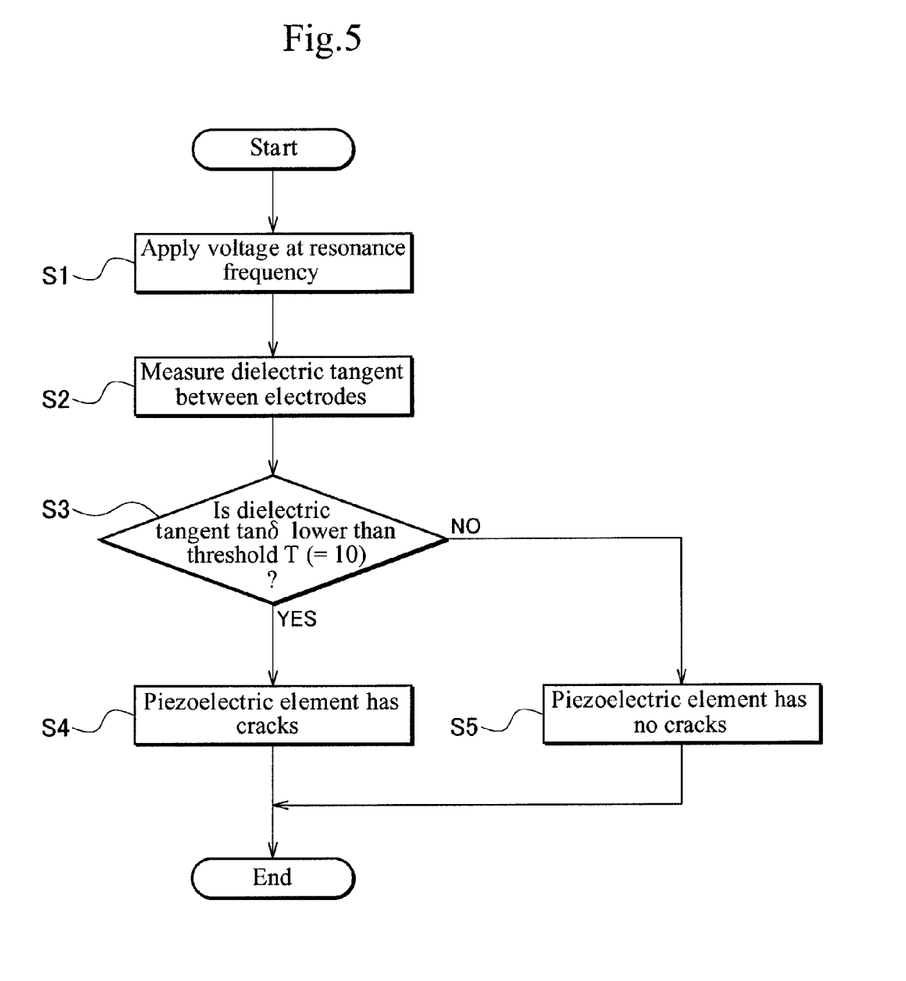
FIG. 5 is a flowchart illustrating a method of detecting cracks in a piezoelectric element according to the first embodiment of the present invention.

FIG. 5 is a flowchart illustrating a method of detecting cracks in a piezoelectric element according to the first embodiment.

The method uses the crack detecting apparatus 1 of FIGS. 1 and 4 and detects cracks, if any, in the piezoelectric element 5 according to a dielectric tangent of the piezoelectric element 5 measured with a voltage at the resonance frequency of the piezoelectric element 5. The piezoelectric element 5 tested according to the method has dimensions of about 1 mm in longitudinal length, about 1.2 mm in width, and about 0.1 mm in thickness and has a resonance frequency of about 1.4 MHz in a state attached as the piezoelectric actuator 11 to the head suspension 3.

To detect cracks in the piezoelectric element 5, the head suspension 3 with the piezoelectric element 5 is set at a predetermined position on a stage (not illustrated) and the measuring cables 57 and 59 of the crack detecting apparatus 1 are connected to the terminals 23 at the second end of the wiring pattern 19 of the flexure 15. In this state, steps of the flowchart of FIG. 5 are carried out.

In step S1 as a voltage applying step, the measuring power source 61 of the measuring unit 49 applies a measuring voltage at the resonance frequency of the piezoelectric element 5 to the piezoelectric element 5.

According to the embodiment, the measuring voltage is 500 mV and the frequency thereof is 1.4 MHz. It is preferable that the measuring voltage is applied by changing (sweeping) the frequency of the voltage step by step within a range around the resonance frequency of the piezoelectric element 5, to deal with variations in the resonance frequency of the piezoelectric element 5 due to production allowance.

In step S2 as a measuring step, the measuring part 63 of the measuring unit 49 measures, according to a current created by the measuring voltage, a dielectric tangent. The measured dielectric tangent is sent to the processing unit 51.

In step S3 as a crack detecting step, the processing unit 51 compares the measured dielectric tangent with the threshold T. According to the embodiment, the threshold T is 10, and therefore, the processing unit 51 checks to see if the measured dielectric tangent is less than 10, i.e., if the measured dielectric tangent is of one digit or two digits.

Figure 6:
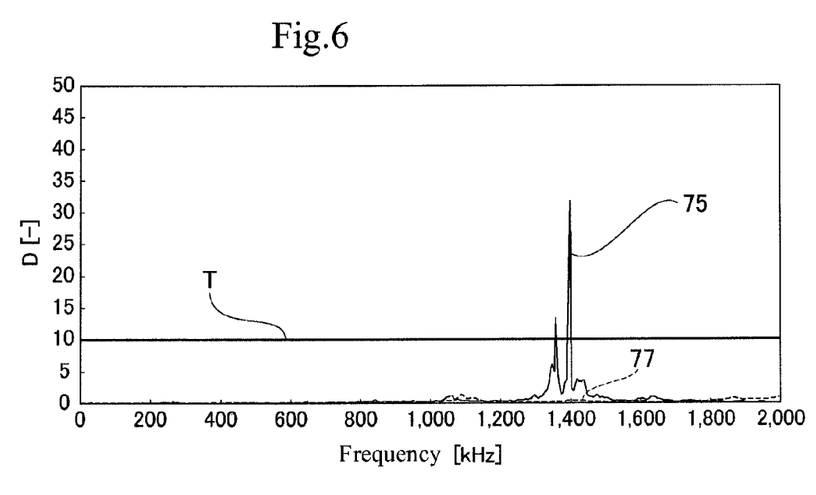
FIG. 6 is a graph illustrating a relationship between measured dielectric tangents of piezoelectric elements and the threshold.

FIG. 6 is a graph illustrating a relationship between measured dielectric tangents of piezoelectric elements and the threshold as dielectric tangent-frequency curves of the piezoelectric elements. In FIG. 6, an ordinate represents the dielectric tangent and an abscissa represents frequency.

The dielectric tangent under the voltage at the resonance frequency of the piezoelectric element 5 without cracks is far above the threshold of 10, as indicated with a segment 75 in FIG. 6. If the piezoelectric element 5 has cracks, the dielectric tangent thereof is far below the threshold of 10. The details of this will be explained later.

If the dielectric tangent under the voltage at the resonance frequency is of one digit, i.e., lower than 10, the processing unit 51 determines that the piezoelectric element 5 has cracks in step S4. If the dielectric tangent under the voltage at the resonance frequency is of two digits, i.e., higher than 10, the processing unit 51 determines that the piezoelectric element 5 has no cracks in step S5.

When the frequency of the measuring voltage is changed step by step, a peak value of dielectric tangent measured in the frequency range is used as a dielectric tangent at the resonance frequency of the piezoelectric element 5.

In this way, the crack detecting method according to the embodiment is capable of easily and surely detecting cracks in the piezoelectric element 5 according to a dielectric tangent at the resonance frequency of the piezoelectric element 5.

The principle of detecting cracks in a piezoelectric element according to a dielectric tangent will be explained.

Figure 7A:
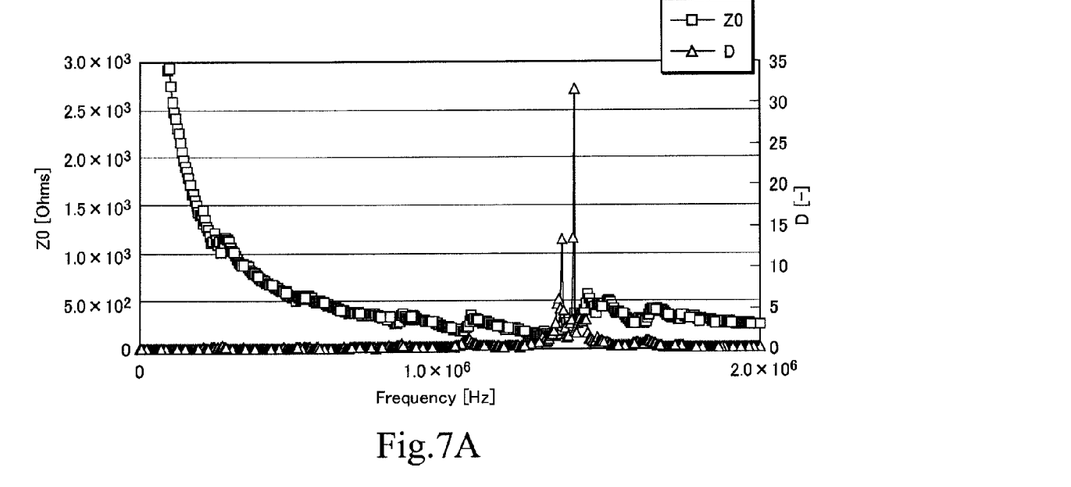
Figure 7B:
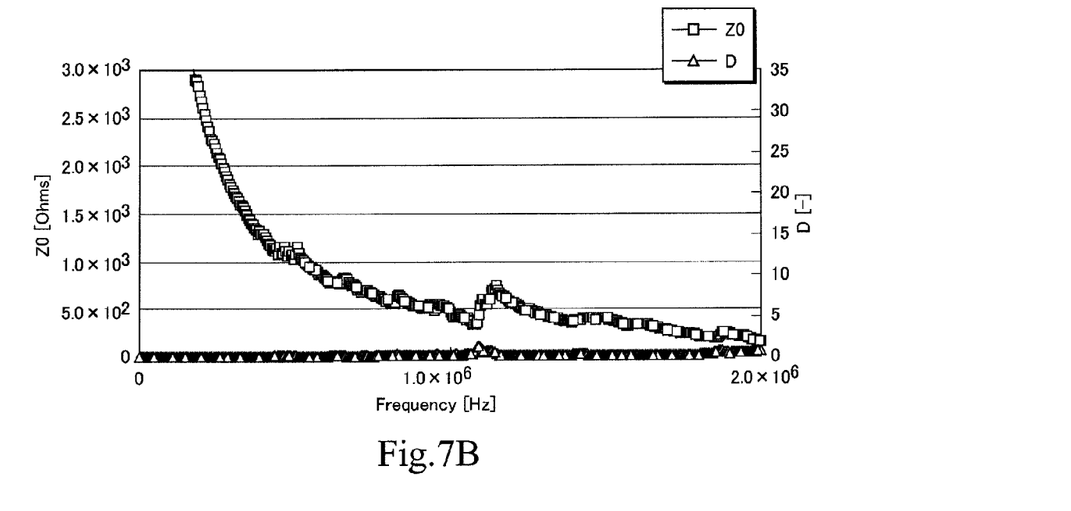

FIGS. 7A and 7B are graphs illustrating an impedance characteristic pattern (an impedance-frequency characteristic pattern) and a dielectric tangent characteristic pattern (a dielectric tangent-frequency characteristic pattern) of piezoelectric elements with respect to frequencies including a resonance frequency as impedance-dielectric tangent-frequency curves thereof, in which FIG. 7A is without cracks and FIG. 7B is with cracks. In FIGS. 7A and 7B, a left ordinate represents impedance (Z0), a right ordinate represents dielectric tangent (D), and an abscissa represents frequency.

The data of FIGS. 7A and 7B are obtained by applying, to piezoelectric element samples, a measuring voltage of about 500 mV at frequency that is changed step by step at intervals of about 5 kHz within the range of about 100 Hz to 2 MHz. At each frequency, the impedance and dielectric tangent of each sample are measured to plot the graphs of FIGS. 7A and 7B. For the measurement, the measuring unit 49 of the crack detecting apparatus 1 according to the embodiment is used.

In FIG. 7A, the piezoelectric element without cracks generally demonstrates a current phase of −90 degrees with respect to a voltage phase at frequencies lower than the resonance frequency and a current phase of +90 degrees with respect to a voltage phase at frequencies between the resonance frequency and an antiresonance frequency (a phase inversion region). Thereafter, it returns to −90 degrees at frequencies exceeding the antiresonance frequency.

The dielectric tangent curve shows a large peak in the phase inversion region compared with a region lower than the resonance frequency and a region higher than the antiresonance frequency.

On the other hand, the piezoelectric element with cracks of FIG. 7B shows no large peak in the dielectric tangent curve, although it demonstrates a phase inversion region like the piezoelectric element without cracks.

In this way, a concept is established in the phase inversion region that the higher the dielectric tangent the better the quality of the piezoelectric element. This is quite contrary to a common concept that the lower the dielectric tangent the better the quality of the piezoelectric element. It is understood that the dielectric tangent of a piezoelectric element has a large peak or no peak depending on whether or not the piezoelectric element has cracks. Based on this principle, the crack detecting method and apparatus according to the present invention measure a dielectric tangent of a given piezoelectric element under a voltage at a resonance frequency of the piezoelectric element in a phase inversion region of the piezoelectric element, and according to the measured dielectric tangent, detect if the piezoelectric element has cracks.

Setting the threshold T for dielectric tangent according to the embodiment will be explained.

Figure 8:
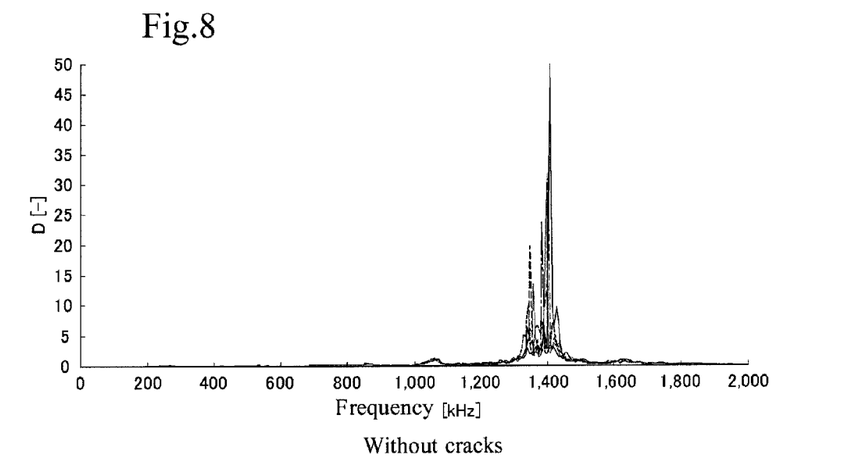
FIG. 8 is a graph illustrating dielectric tangent characteristic patterns of piezoelectric elements without cracks with respect to frequencies including a resonance frequency.
Figure 9:
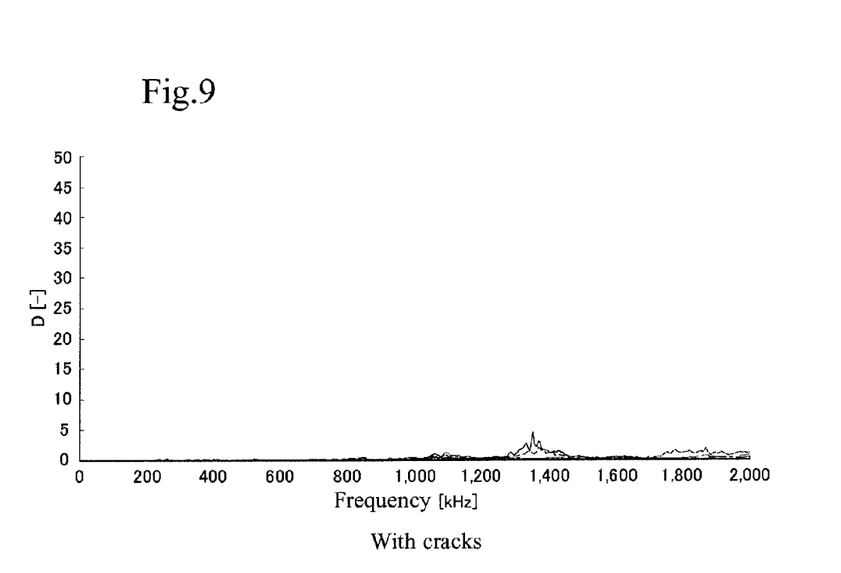
FIG. 9 is a graph illustrating dielectric tangent-frequency characteristic patterns of piezoelectric elements with cracks with respect to frequencies including a resonance frequency.
Figure 10:
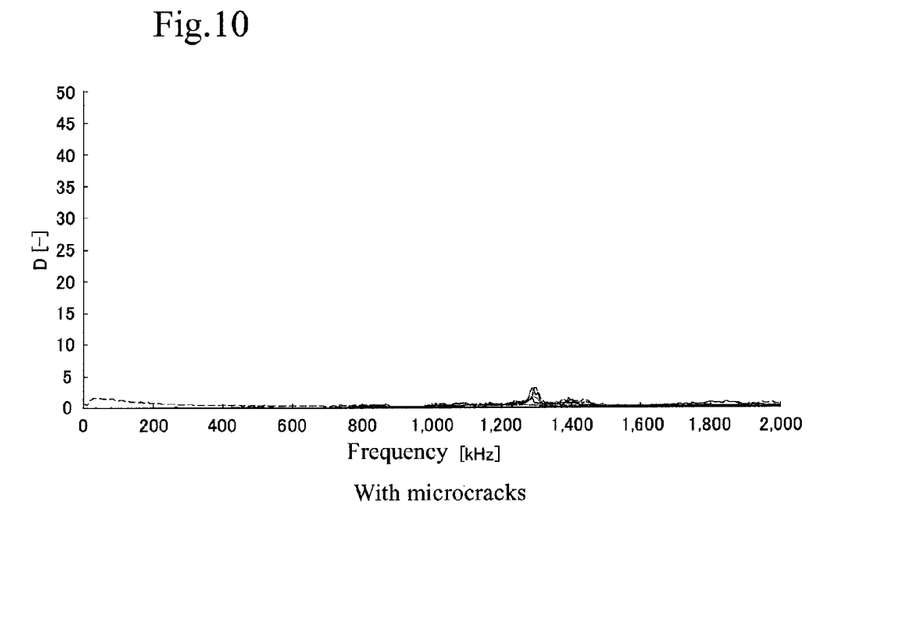
FIG. 10 is a graph illustrating dielectric tangent-frequency characteristic patterns of piezoelectric elements with microcracks with respect to frequencies including a resonance frequency.

FIGS. 8 to 10 are graphs illustrating dielectric tangent characteristic patterns or curves (dielectric tangent-frequency characteristic patterns) of piezoelectric element samples with respect to frequencies including a resonance frequency, in which FIG. 8 is of those without cracks, FIG. 9 is of those with cracks (clearly recognizable from the appearance), and FIG. 10 is of those with microcracks (unrecognizable or hardly recognizable from the appearance).

The data of FIGS. 8 to 10 are collected like those of FIGS. 7A and 7B. In FIGS. 8 to 10, an ordinate represents dielectric tangent and an abscissa represents frequency. The piezoelectric element samples of FIGS. 8 to 10 are the same as those used for the crack detecting method.

Figure 11:
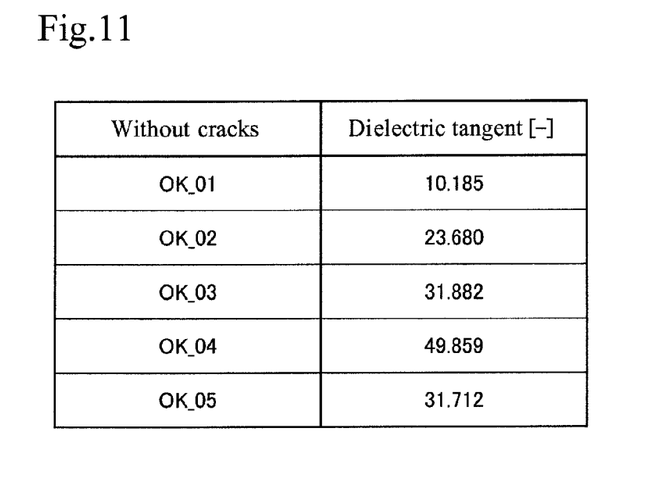
FIG. 11 is a table listing peak values of the dielectric tangents of FIG. 8.
Figure 12:
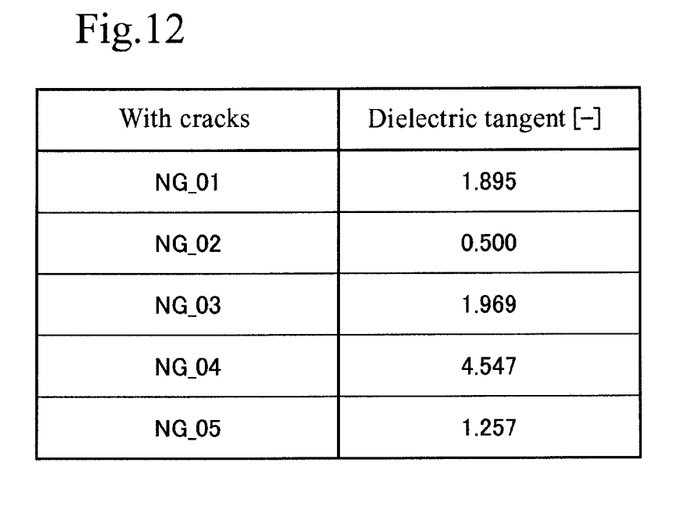
FIG. 12 is a table listing peak values of the dielectric tangents of FIG. 9.
Figure 13:
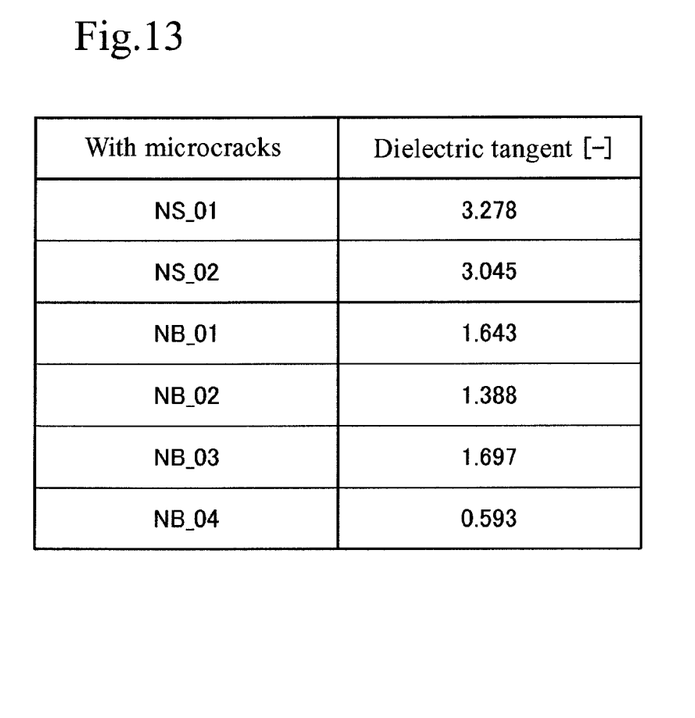
FIG. 13 is a table listing peak values of the dielectric tangents of FIG. 10.

FIGS. 11 to 13 are tables listing peak values of the dielectric tangents of FIGS. 8 to 10. In FIG. 13, a piezoelectric element sample marked with "NS" has microcracks that are unrecognizable from the appearance and that marked with "NB" has microcracks that are difficult to recognize from the appearance.

In FIGS. 8 and 11, the piezoelectric elements without cracks each have a peak value (a vertex of a peak pattern) larger than 10 in dielectric tangent at the resonance frequency of 1.4 MHz. At other frequencies, the piezoelectric elements without cracks each demonstrate a dielectric tangent of 5 or lower.

On the other hand, the piezoelectric elements with cracks illustrated in FIGS. 9, 10, 12, and 13 each have no large peak (a vertex of a peak pattern) at the resonance frequency, and at all frequencies, each show a dielectric tangent below 5.

Namely, the piezoelectric elements with cracks demonstrate no large peak value in dielectric tangent at the resonance frequency regardless of the size of cracks, and at all frequencies, dielectric tangent values lower than 5.

Accordingly, it may be satisfactory to set the dielectric tangent threshold T at the resonance frequency to 10. With this threshold, it is possible to test if a given piezoelectric element has cracks. Namely, if the dielectric tangent of a given piezoelectric element measured with a voltage at the resonance frequency is lower than the threshold T, it is determined that the piezoelectric element has microcracks. Such microcracks are generally difficult to detect because they only cause a capacitance difference that falls within a production allowance.

The threshold T may be set between a peak value of dielectric tangents measured at a resonance frequency on piezoelectric elements without cracks and a peak value of dielectric tangents measured at the resonance frequency on piezoelectric elements with cracks. Namely, the threshold T may be set to a value smaller than 10 and may be stochastically calculated.

Effect of the first embodiment will be summarized.

The crack detecting method according to the embodiment detects cracks in the piezoelectric element 5 interposed between the pair of electrodes 37 and 39 and deforms according to a voltage applied thereto through the electrodes 37 and 39. The method includes steps of applying a voltage at least at a resonance frequency of the piezoelectric element 5 to the piezoelectric element 5 through the electrodes 37 and 39 (the voltage applying step), measuring a dielectric tangent between the electrodes 37 and 39 (the measuring step), and according to the measured dielectric tangent, detecting if the piezoelectric element 5 has cracks (the crack detecting step).

The measured dielectric tangent of the piezoelectric element 5 at the resonance frequency has a large peak or no peak depending on whether or not the piezoelectric element 5 has cracks. Accordingly, the crack detecting method according to the embodiment easily and surely detects cracks in the piezoelectric element 5, if any, according to the dielectric tangent measured under the voltage at the resonance frequency.

The crack detecting method according to the embodiment determines that the piezoelectric element 5 has cracks if the dielectric tangent measured under the voltage at the resonance frequency is lower than the threshold T in the crack detecting step. Namely, only by measuring a dielectric tangent at a resonance frequency of a given piezoelectric element, the method is capable of easily and surely detecting if the piezoelectric element has cracks.

According to the embodiment, the threshold T for dielectric tangent is set between a peak dielectric tangent measured at a resonance frequency on piezoelectric element samples without cracks and a peak dielectric tangent measured at the resonance frequency on piezoelectric element samples with cracks. Accordingly, the embodiment is capable of easily and surely detect if a given piezoelectric element has cracks.

According to the embodiment, the threshold T for dielectric tangent is set to 10. Only by checking to see if the dielectric tangent of a given piezoelectric element measured at the resonance frequency thereof is of one digit or two digits, the embodiment is capable of simply, easily, and surely detecting if the piezoelectric element has cracks.

According to the embodiment, the resonance frequency of the piezoelectric element 5 is that of the piezoelectric element 5 assembled in the piezoelectric actuator 11 of the head suspension 3. Accordingly, the embodiment is capable of easily and surely detecting whether or not the piezoelectric element 5 in the piezoelectric actuator 11 has cracks.

According to the embodiment, a voltage is applied through the flexure 15 to the piezoelectric element 5, and therefore, the embodiment is capable of easily and surely testing if the piezoelectric element 5 arranged in the head suspension 3 has cracks.

The crack detecting apparatus 1 according to the embodiment includes the measuring power source 61 that applies a voltage of at least a resonance frequency of the piezoelectric element 5 to the piezoelectric element 5, the measuring part 63 that measures a dielectric tangent between the pair of electrodes 37 and 39 under the applied voltage, and the processing unit 51 (detecting unit) that detects if there are cracks in the piezoelectric element 5 according to the measured dielectric tangent.

The crack detecting apparatus 1 easily and surely carries out the crack detecting method (FIG. 5) to detect whether or not the piezoelectric element 5 has cracks.

The processing unit 51 includes the storage part 71 that stores the threshold T to be compared with a dielectric tangent peak value and the determination part 69 that determines that the piezoelectric element 5 has cracks if the peak dielectric tangent of the piezoelectric element 5 is lower than the threshold T.

With the use of the threshold T, the crack detecting apparatus 1 is capable of easily and surely detecting cracks, if any, in the piezoelectric element 5.

An apparatus for detecting cracks in a piezoelectric element according to the second embodiment of the present invention will be explained with reference to FIG. 14. A method of detecting cracks according to the second embodiment will be explained as functions of the apparatus for detecting cracks.

Figure 14:
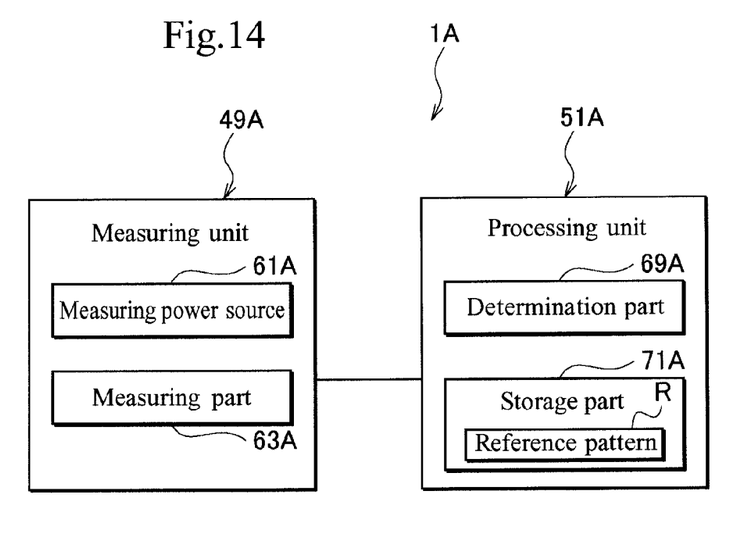
FIG. 14 is a schematic view illustrating an apparatus for detecting cracks in a piezoelectric element according to a second embodiment of the present invention.

FIG. 14 is a schematic view illustrating an apparatus for detecting cracks in a piezoelectric element according to a second embodiment of the present invention. The crack detecting apparatus 1A according to the second embodiment illustrated in FIG. 14 is basically the same as the crack detecting apparatus 1 illustrated in FIGS. 1 and 4, and therefore, parts of the apparatus 1A corresponding to those of the apparatus 1 are represented with the same reference marks plus "A" to omit the repeated explanation thereof.

The crack detecting apparatus 1A according to the second embodiment detects if a given piezoelectric element has cracks by directly comparing a dielectric tangent pattern of the piezoelectric element with a reference dielectric tangent pattern instead of comparing a dielectric tangent of the piezoelectric element with the threshold T.

According to the second embodiment, the crack detecting apparatus 1A has a measuring unit 49A including a measuring power source 61A. The measuring power source 61A applies a measuring voltage of, for example, 500 mV to a test piezoelectric element by changing the frequency of the measuring voltage at intervals of 5 kHz within a range of 100 Hz to 2 MHz. A measuring part 63A in the measuring unit 49A measures a dielectric tangent of the test piezoelectric element at each frequency and sends the measured dielectric tangent to a determination part 69A of a processing unit 51A.

Namely, the measuring power source 61A applies a measuring voltage to a piezoelectric element at frequencies including the resonance frequency of the piezoelectric element in a voltage applying step and the measuring part 63A continuously measures the dielectric tangent of the piezoelectric element at each frequency in a measuring step.

The determination part 69A of the processing unit 51A creates a dielectric tangent characteristic pattern like those illustrated in FIGS. 8 to 10 according to the dielectric tangents measured at the changed frequencies and compares the pattern with a reference dielectric tangent pattern R stored in a storage part 71A of the processing unit 51A in a crack detecting step.

The reference dielectric tangent pattern R is prepared in advance from dielectric tangents measured on piezoelectric element samples without cracks. The reference pattern R may be, for example, a segment 75 illustrated in FIG. 6.

If the created dielectric tangent pattern does not agree with the reference pattern R, i.e., if the created pattern includes no peak pattern, the determination part 69A determines that the tested piezoelectric element has cracks.

The dielectric tangent pattern of a tested piezoelectric element is not always required to completely agree with the reference pattern R when determining that the tested piezoelectric element has no cracks. For example, feature points of the dielectric tangent pattern of the tested piezoelectric element may be extracted and compared with those of the reference pattern R when determining whether or not the tested piezoelectric element has cracks. Alternatively, an allowable range of the reference pattern R may stochastically be computed, and if the dielectric tangent pattern of the tested piezoelectric element is within the allowable range, it is determined that the dielectric tangent pattern of the tested piezoelectric element agrees with the reference pattern R.

The reference pattern R may be prepared from piezoelectric elements with cracks. In this case, the reference pattern R may be, for example, a segment 77 of FIG. 6. In this case, if the dielectric tangent pattern of a tested piezoelectric element agrees with the reference pattern R, it is determined that the tested piezoelectric element has cracks.

In this case, the dielectric tangent pattern of a tested piezoelectric element is not always required to completely agree with the reference pattern R as explained above.

The dielectric tangent pattern of a tested piezoelectric element and the reference pattern R are not required to be prepared for an entire frequency range. They may be prepared for a limited frequency range around the resonance frequency of the piezoelectric element at which a peak pattern appears.

The second embodiment provides the same effect as the first embodiment. In addition, the second embodiment easily and surely detects if a given piezoelectric element has cracks by directly comparing the dielectric tangent pattern of the piezoelectric element with the reference dielectric tangent pattern R. This is because the dielectric tangent pattern of the piezoelectric element includes a large peak or no peak depending on whether or not the piezoelectric element has cracks.

According to the first and second embodiments, the piezoelectric element 5 includes a pair of piezoelectric bodies 29 and 31. The present invention is also applicable to a piezoelectric element including a single piezoelectric body. In this case, each of the electrode 37 and 39 may be a single plate.

According to the embodiments, the crack detecting method and apparatus detect cracks in the piezoelectric element 5 of the piezoelectric actuator 11 arranged on the head suspension 3. The present invention is also applicable to detect cracks in piezoelectric elements of any other piezoelectric actuators.

According to the embodiments, the crack detecting apparatus uses the measuring power source 61 of the measuring unit 49, i.e., an LCR meter, to apply a voltage to the piezoelectric element 5. The voltage applied to the piezoelectric element 5 may be supplied from any other unit such as a probe unit to secure measuring stability.

According to the embodiments, the example of the piezoelectric element 5 has the resonance frequency of about 1.4 MHz. The resonance frequency may be changed according to the dimensions, configurations and the like of the piezoelectric element 5 and head suspension 3. If the resonance frequency is changed, a range for the change of the frequency of the measuring voltage may be changed.

According to the embodiments, the intervals for the change of the frequency of the measuring voltage is about 5 kHz and the measuring voltage is about 500 mV. The intervals and the measuring voltage may be changed according to a required accuracy or the like for the detection of cracks.

What is claimed is:

1. A method of detecting one or more cracks in a piezoelectric element of a micro actuator, the piezoelectric element interposed between a pair of electrodes formed on respective first and second surfaces of the piezoelectric element and the piezoelectric element deforming according to a voltage applied thereto through the pair of electrodes, comprising:
   detecting if there are cracks in the piezoelectric element before the micro actuator is installed into a device needing the micro actuator and initiates operation in the device, said detecting comprising:
   applying a voltage at a resonance frequency of the piezoelectric element to the piezoelectric element through the pair of electrodes;
   measuring a dielectric tangent between the pair of electrodes when said voltage at the resonance frequency is applied to the piezoelectric element; and
   determining that cracks in the piezoelectric element are present when a peak at said resonance frequency of the measured dielectric tangent between the pair of electrodes is less than a threshold.

2. The method of claim 1, wherein the threshold is set between a peak dielectric tangent value measured at the resonance frequency on piezoelectric element samples without cracks and a peak dielectric tangent value measured at the resonance frequency on piezoelectric element samples with cracks.

3. The method of claim 2, wherein the threshold is 10.

4. The method of claim 1, wherein said applying the voltage at the resonance frequency to the piezoelectric element one time is achieved by changing and sweeping the frequency of the voltage in a frequency band including the resonance frequency,
wherein the measuring step is achieved by continuously measuring dielectric tangents in the frequency band, and
wherein the crack detecting step is carried out by forming a dielectric tangent pattern according to the measured dielectric tangents, comparing the dielectric tangent pattern with a reference pattern, and checking to see if the dielectric tangent pattern has a peak pattern.

5. The method of claim 1, wherein the piezoelectric element forms a piezoelectric actuator that is arranged between a base part and a driven part and drives the driven part relative to the base part according to the deformation of the piezoelectric element, and the resonance frequency is a resonance frequency of the piezoelectric element in the piezoelectric actuator.

6. The method of claim 5, wherein the driven part is a load beam of a head suspension, one of the pair of electrodes of the piezoelectric element is connected to a wiring member of the head suspension, and the voltage is applied through the wiring member to the piezoelectric element.

7. An apparatus for detecting one or more cracks in a piezoelectric element of a micro actuator, the piezoelectric element interposed between a pair of electrodes formed on respective first and second surfaces of the piezoelectric element and the piezoelectric element deforming according to a voltage applied thereto through the pair of electrodes, comprising:
a setting portion to which the micro actuator is set before the micro actuator is installed into a device needing the micro actuator and initiates operation in the device;
a voltage applying unit that applies a voltage at a resonance frequency of the piezoelectric element to the piezoelectric element through the pair of electrodes;
a measuring unit that measures a dielectric tangent between the pair of electrodes when said voltage at the resonance frequency is applied to the piezoelectric element; and
a detecting unit that detects that cracks in the piezoelectric element are present when a peak at said resonance frequency of the measured dielectric tangent between the pair of electrodes is less than a threshold.

8. The apparatus of claim 7, wherein the detecting unit includes a storage part that stores a threshold for dielectric tangent and a determination part that determines that there are cracks in the piezoelectric element if the measured dielectric tangent is lower than the threshold.

9. The apparatus of claim 8, wherein the threshold is set between a peak dielectric tangent value measured at the resonance frequency on piezoelectric element samples without cracks and a peak dielectric tangent value measured at the resonance frequency on piezoelectric element samples with cracks.

10. The apparatus of claim 8, wherein the threshold is 10.

11. The apparatus of claim 7, wherein the voltage applying unit applies the voltage to the piezoelectric element one time by changing and sweeping the frequency of the voltage in a frequency band including the resonance frequency,
wherein the measuring unit continuously measures dielectric tangents in the frequency band, and
wherein the detecting unit includes a storage part that stores a reference pattern prepared from dielectric tangents of piezoelectric element samples and a determination part that forms a dielectric tangent pattern according to the measured dielectric tangents, compares the dielectric tangent pattern with the reference pattern, and checks to see if the dielectric tangent pattern has a peak pattern, thereby determining whether or not there are cracks in the piezoelectric element.

12. The method of claim 1, wherein said applying the voltage at the resonance frequency to the piezoelectric element one time is achieved by changing and sweeping the frequency of the voltage in a frequency band including the resonance frequency; and
wherein the measuring step is achieved by continuously measuring dielectric tangents in the frequency band.

13. The apparatus of claim 7, wherein the voltage applying unit applies the voltage to the piezoelectric element one time by changing and sweeping the frequency of the voltage in a frequency band including the resonance frequency; and
wherein the measuring unit continuously measures dielectric tangents in the frequency band.

14. A method of detecting one or more cracks in a piezoelectric element interposed between a pair of electrodes, comprising steps of: deforming the piezoelectric element according to a voltage applied thereto through the pair of electrodes; and measuring a dielectric tangent between the pair of electrodes; and wherein all deforming of the piezoelectric element occurring during said measuring is responsive to applying only one time a first voltage at a resonance frequency of the piezoelectric element to the piezoelectric element through the pair of electrodes, said first voltage being applied at a first time; wherein said measuring the dielectric tangent is based upon said one time applying of the first voltage at said first time; and further comprising determining that cracks in the piezoelectric element are present when a peak at said resonance frequency of the measured dielectric tangent between the pair of electrodes is less than a threshold.

* * * * *